(12) United States Patent
Tung

(10) Patent No.: US 7,846,411 B2
(45) Date of Patent: Dec. 7, 2010

(54) CALCIUM PEROXYPHOSPHATES AND USE THEREOF IN DENTAL COMPOSITIONS

(75) Inventor: Ming Tung, Gaithersburg, MD (US)

(73) Assignee: ADA Foundation, Gaithersburg, MD (US)

( * ) Notice: Subject to any disclaimer, the term of this patent is extended or adjusted under 35 U.S.C. 154(b) by 1674 days.

(21) Appl. No.: 10/868,880

(22) Filed: Jun. 17, 2004

(65) Prior Publication Data
US 2005/0281759 A1 Dec. 22, 2005

(51) Int. Cl.
| A61K 8/00 | (2006.01) |
| A61K 8/22 | (2006.01) |
| A61K 8/24 | (2006.01) |
| A61K 33/06 | (2006.01) |
| A61K 31/66 | (2006.01) |
| A61Q 11/00 | (2006.01) |

(52) U.S. Cl. .................. 423/308; 423/299; 423/309; 424/49; 424/53; 424/57

(58) Field of Classification Search .................. 423/308, 423/309; 424/49, 53
See application file for complete search history.

(56) References Cited

U.S. PATENT DOCUMENTS

| 3,036,887 A | 5/1962 | Beer et al. |
| 3,085,856 A | 4/1963 | Lake et al. |
| 3,666,399 A * | 5/1972 | Castrantas .................. 8/111 |
| 4,041,149 A * | 8/1977 | Gaffar et al. .................. 424/57 |
| 4,309,410 A | 1/1982 | Gaffar |
| 5,037,639 A | 8/1991 | Tung |
| 5,624,906 A | 4/1997 | Vermeer |
| 5,648,064 A | 7/1997 | Gaffar et al. |
| 5,698,182 A | 12/1997 | Prencipe et al. |
| 5,770,182 A | 6/1998 | Fischer |
| 5,776,437 A | 7/1998 | Burgess et al. |
| 5,820,852 A | 10/1998 | Burgess et al. |
| 5,849,269 A | 12/1998 | Burgess et al. |
| 5,851,514 A | 12/1998 | Hassan et al. |
| 5,902,568 A | 5/1999 | Ryles et al. |
| 5,967,155 A | 10/1999 | Marcon |
| 6,102,050 A | 8/2000 | Marcon |
| 6,221,341 B1 | 4/2001 | Montgomery |
| 6,290,935 B1 | 9/2001 | Masters et al. |
| 6,303,104 B1 | 10/2001 | Winston et al. |
| 6,419,905 B1 | 7/2002 | Alvarez Hernandez |
| 6,447,757 B1 * | 9/2002 | Orlowski et al. .............. 424/53 |
| 6,521,215 B2 | 2/2003 | Okay |

OTHER PUBLICATIONS

Zhou, et al., "Studies on regular changes of quality under different treatments between early and late cropping seasons in South-China Indica rice", Acta Agronomica Sinica, 2003 (vol. 29) (No. 2) 225-229. Abstract only. (Abstract from CAB Abstracts, http://www.cababstractsplus.org/google/abstract.asp?AcNo=20043045255, p. 1-2) Article: Mar. 2003.*
Nathanson, D., "Vital Tooth Bleaching: Sensitivity and Pulpal Considerations," JADA, vol. 128 (1997).
Attin, T. et al., "Susceptibility of Enamel Surfaces to Demineralization after Application of Fluoridated Carbamide Peroxide Gels," Caries Res. Mar.-Apr.; vol. 37(2), pp. 93-99 (2003).
Can. J. Chem., vol. 81, pp. 156-160 (2003).
Such, J. E., "Peroxophosphoric Acid & Peroxophosphates", Mellor's Comprehensive Treatise on Inorganic and Theoretical Chemistry, vol. VIII, Supp. III, Longmana, London (1971).
Schumb, W.C. et al., "Hydrogen Peroxide," Reinhold Publishing Corporation, New York, N.Y. (1955).
International Search Report and Written Opinion in International Application PCT/US05/13028 (Sep. 8, 2004).

* cited by examiner

Primary Examiner—Frederick Krass
Assistant Examiner—Lezah W Roberts
(74) Attorney, Agent, or Firm—Banner & Witcoff, LTD.

(57) ABSTRACT

Calcium peroxyphosphate compounds and dental compositions comprising these compounds that combine both whitening/stain removal of teeth with remineralization are disclosed. The calcium peroxyphosphate compounds are capable of releasing, in an aqueous environment, whitening and remineralization effective amounts of calcium ion, phosphate ion, and active oxygen. Preferred compounds are calcium peroxymonophosphate or calcium diperoxymonophosphate compounds. These compounds may be used in humans and other animals, including other mammals.

23 Claims, No Drawings

CALCIUM PEROXYPHOSPHATES AND USE THEREOF IN DENTAL COMPOSITIONS

FIELD OF THE INVENTION

The present invention relates to calcium peroxyphosphate compounds, methods for the preparation thereof, and the use thereof in dental compositions for whitening, mineralizing, and/or fluoridating teeth. These dental compositions advantageously whiten teeth while simultaneously remineralizing them to prevent and/or repair weaknesses including dental caries, exposed dentin tubules, and voids resulting from stain removal.

BACKGROUND OF THE INVENTION

A tooth is comprised of an outer hard enamel protective layer and an inner dentin layer. The outer enamel layer is naturally either opaque white or slightly off-white in color. It is composed of apatite mineral crystals that are somewhat porous. Without being bound by theory, it is believed that the porous nature of the enamel layer permits staining agents and discoloring substances to permeate into the enamel and discolor a tooth.

Dentin, the inner bony part of the tooth, contains thousands of microscopic tubules. On the crown end of the tooth, the dentin tubule ends are normally sealed by the enamel. These dentin tubules pass all the way through the dentin from the enamel-sealed crown end to the pulp chamber. On the root end of the tooth, these tubules are also sealed by a bony material called cementum. However, if either the enamel-sealed crown ends or the cementum-sealed root ends of the dentin tubules become exposed, fluid easily travels through the tubules, causing hypersensitivity and/or pain. Undesirable exposure of dentin tubules may result from mechanical abrasion, caries, chemical treatment (e.g., whitening agents), and other factors.

Plaques are a major cause of both dental decay and inflammatory periodontal disease. These plaques can contain 250 or more separate microbial species. They use sugars and other fermentable carbohydrates to produce acids, which cause demineralization of the tooth surface, and polymers, with which the microbial organisms bind themselves to the tooth surface. In its initial stages, the formation of a carious lesion is not readily apparent. However, with prolonged and repeated demineralization by plaque-created acids, a cavity will ultimately become visible.

Peroxide has been used as an oxidizing agent for whitening teeth as well as for the treatment of various forms of stomatitis and gingivitis. See, e.g., U.S. Pat. No. 5,820,852. When applied for extended periods at high concentrations, oxidizing agents such as hydrogen peroxide and urea peroxide (carbamide) have proven effective for removing extrinsic and intrinsic stains as well as for brightening the overall shade and color of teeth. Unfortunately, the bleaching process for removing stains can simultaneously reduce the microhardness of enamel and dentin, cause post-treatment tooth sensitivity, and/or increase tooth susceptibility to demineralization. See Nathanson, D.; "*Vital Tooth Bleaching: Sensitivity and Pulpal Considerations*," JADA, 128 (April 1997); and Attin, T. et aL, "Susceptibility of Enamel Surfaces to Demineralization after Application of Fluoridated Carbamide Peroxide Gels," Caries Res. March-April; 37(2):93-9 (2003).

Various dental products have been formulated to address plaque formation and tooth whitening. For 5, U.S. Pat. No. 6,290,935 describes an oral composition comprising a peroxide first component (e.g., hydrogen peroxide, peroxydiphosphate, urea peroxide (carbamide), metal peroxides such as calcium peroxide, and salts of perborate, persilicate, perphosphate, and percarbonate) and a silicate clay activator second component, implanted with Fe ions. U.S. Pat. No. 6,521,215 describes compositions comprising a whitening agent comprising >10% peroxide (e.g., urea peroxide (carbamide) or hydrogen peroxide) and a soluble calcium phosphate remineralizing agent (e.g., monocalcium phosphate, anhydrous dicalcium phosphate, tricalcium phosphate, or tetracalcium phosphate). U.S. Pat. No. 6,419,905 describes a dental bleaching composition comprising urea peroxide (carbamide), xylitol, a potassium salt (e.g., potassium pyrophosphate or potassium phosphate), and a fluoride salt (e.g., sodium monofluorophosphate). U.S. Pat. No. 6,221,341 describes compositions for whitening teeth and/or having antimicrobial activity. These compositions comprise an acyl group (or functionally similar group) source or precursor and a peroxide source or precursor (e.g., urea peroxide (carbamide), sodium percarbonate, sodium perborate, calcium peroxide, magnesium peroxide, or sodium peroxide), which react in an aqueous environment to generate a peroxyacid (e.g., peroxyacetic acid). The compositions have a pH>5.2 to avoid solubilizing calcium in the tooth enamel or otherwise demineralizing the tooth. The peroxyacetic acid, which is unstable at this pH range, is therefore generated in situ by the above-described reaction. U.S. Pat. Nos. 6,102,050 and 5,967,155 describe dental flosses that administer various compounds to interproximal and subgingival dental areas for purposes such as whitening, remineralization, and desensitization. In addition to titanium dioxide as a whitening agent, other ingredients that may be incorporated into the floss include desensitizing agents (e.g., calcium nitrate, calcium hydroxide, or dibasic calcium phosphate), fluorides (e.g., calcium fluoride, sodium monofluorophosphate, aluminum mono- and di-fluorophosphate), peroxide compounds (e.g., calcium peroxide and sodium carbonate peroxide), and abrading agents (e.g., calcium). The fluoride compounds are taught to be catalytically active in remineralizing or precipitating calcium and phosphate compounds, found in saliva, onto teeth.

U.S. Pat. No. 5,902,568 describes compositions comprising hydrogen peroxide or a precursor (e.g., sodium perborate, persilicate, percarbonate, perphosphate, calcium peroxide, or sodium peroxide) and bicarbonate salt components that are separated from one another to prevent their premature reaction prior to use. The compositions have a pH range of 9-12, based on the combined components, to increase whitening. The hydrogen peroxide or precursor component may contain phosphoric acid. The bicarbonate salt component may contain a carbonate (e.g., calcium carbonate). In one or both of the peroxide or bicarbonate salt components, fluoride (e.g., stannous monofluorophosphate or sodium monofluorophosphate) may be present. U.S. Pat. No. 5,851,514 describes a whitening composition containing both a peroxide compound (e.g., calcium peroxide, hydrogen peroxide, urea peroxide (carbamide), glyceryl peroxide, or benzoyl peroxide) and an abrasive compound (e.g., dicalcium phosphate compounds such as dicalcium phosphate-dihydrate and anhydrous dicalcium phosphate or calcium pyrophosphate, preferably a high beta phase calcium pyrophosphate). U.S. Pat. No. 5,770,182 describes high viscosity sustained release dental compositions for treating tooth surfaces with whitening agents (e.g., urea peroxide) or fluorides (e.g., sodium fluoride). These components are included in a high viscosity matrix material (e.g., carboxypolymethylene) and are preferably applied using a dental tray.

U.S. Pat. No. 5,698,182 describes a composition for whitening teeth and inhibiting dental calculus comprising an anti-calculus phosphate salt and calcium peroxide. U.S. Pat. No. 5,648,064 describes a two component dentifrice composition. The composition comprises a peroxygen compound first component (e.g., hydrogen peroxide, peroxydiphosphate, urea peroxide (carbamide), calcium, sodium, strontium, and magnesium peroxide salts, and perphosphate salts) and a manganese coordination complex (e.g., manganese gluconate) second component to activate the peroxygen compound and accelerate the release of active oxygen upon combining with the first component.

U.S. Pat. No. 5,624,906 describes an oral hygiene composition comprising a heteroatom containing alkyl aldonamide compound (e.g., alkoxymethyl gluconamide).

U.S. Pat. No. 6,303,104 describes a two-component composition for whitening and remineralizing teeth. The first component contains an at least partially soluble calcium salt, which may be a soluble calcium salt (e.g., calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, or calcium valerate) and optionally a soluble non-calcium divalent metal salt or an anhydrous calcium phosphate or dicalcium phosphate abrasive. The second component comprises a soluble orthophosphate salt (e.g., monopotassium phosphate) and optionally a fluoride salt (e.g., sodium monofluorophosphate). No peroxide is mentioned. U.S. Pat. Nos. 5,849,269; 5,820,852; and 5,776,437 describe oral compositions comprising a fluoride ion source (e.g., sodium monofluorophosphate), pyrophospate (e.g., tetrasodium pyrophosphate, either anhydrous salt or hydrated), and calcium peroxide. The oral compositions have a pH of 9.0-10.5.

U.S. Pat. No. 5,330,746 describes a composition containing either an anti-plaque agent (e.g., cetylpyridinium chloride) or an anti-hypersensitivity agent (e.g., a strontium salt). The agents are contained in a topically-applied varnish (e.g., a polymethacrylate) to provide their sustained release. The composition may also contain an oxygenating agent (e.g., urea peroxide (carbamide), hydrogen peroxide, peroxyborate, or peroxydiphosphate).

In view of these disclosures, there is an ongoing need in the art for compositions that can both whiten and remineralize teeth and fill voids associated with tooth decay and/or mechanical injury. Especially desired are compositions that comprise a whitening/stain removal agent (e.g., a source of peroxide and/or active oxygen) with sources of calcium ions and phosphate ions to remineralize teeth, thereby filling voids, adding strength, and reducing sensitivity.

SUMMARY OF THE INVENTION

The present invention is directed to calcium peroxyphosphate compounds and methods for the preparation of these compounds. The present invention is also directed to dental compositions comprising calcium peroxyphosphate compounds and methods for using such compositions that combine tooth whitening/stain removal with remineralization to hinder and/or prevent degradation of the tooth structure, normally associated with whitening.

In one embodiment, therefore, the present invention is a calcium peroxyphosphate compound or a hydrate or a peroxyhydrate thereof. In another embodiment, the compound further comprises hydrogen ions and/or hydroxide ions.

In another embodiment, the calcium peroxyphosphate compound is a calcium peroxymonophosphate or calcium diperoxymonophosphate having Formula (I):

$$Ca_qH_x(PHOS)_y(OH)_z \quad \text{(I)}$$

or a hydrate or a peroxyhydrate thereof, wherein q is $½·(3y+z-x)$; x is from 0 to 8; y is an integer from 1 to 3; z is from 0 to 1; x<3y; and PHOS is peroxymonophosphate having the formula $PO_5$ or diperoxymonophosphate having the formula $PO_6$, or wherein said calcium peroxyphosphate compound is a calcium peroxydiphosphate or calcium diperoxydiphosphate compound having Formula (II):

$$Ca_qH_x(DIPHOS) \quad \text{(II)}$$

or a hydrate or a peroxyhydrate thereof, wherein q is $½·(4-x)$; x is from 0 to 3; and DIPHOS is peroxydiphosphate having the formula $P_2O_8$ or diperoxydiphosphate having the formula $P_2O_9$.

In yet another embodiment, the present invention is a tooth whitening and remineralizing composition comprising any of the calcium peroxyphosphate compounds described above that releases, in an aqueous environment, calcium ions, phosphate ions, and active oxygen in combined effective amounts or concentrations to achieve the dual purposes of whitening and remineralization.

In another embodiment, the present invention is a method for whitening and remineralizing teeth. The method comprises applying to the teeth a composition releases, in an aqueous environment, calcium ions, orthophosphate ions, and active oxygen in combined tooth whitening and remineralization effective amounts.

In another embodiment, the present invention is a method for preparing any of the calcium peroxyphosphate compounds described above. The method comprises reacting a peroxy acid with a calcium compound to produce the calcium peroxyphosphate compound. In a preferred embodiment, the calcium peroxyphosphate compound is a calcium peroxymonophosphate compound and the peroxy acid is peroxymonophosphoric acid. In another preferred embodiment, the calcium compound is selected from the group consisting of calcium carbonate, calcium bicarbonate, and calcium hydroxide. In another preferred embodiment, the reaction is carried out at a temperature from about −10° C. to about 20° C.

These and other embodiments of the invention are discussed in the following detailed description.

DETAILED DESCRIPTION OF THE INVENTION

Calcium peroxyphosphates represent a class of compounds capable of releasing active oxygen, calcium ions, and phosphate ions from a single molecule. Such compounds provide both whitening and remineralizing components for oral use. In particular, without being bound by theory, it is believed that as active oxygen removes tooth stains and leaves behind a void, the calcium and phosphate ions that are in close proximity and released from the same parent molecule precipitate to form tooth mineral (i.e., calcium phosphate) and repair the void by such remineralization. Such calcium peroxyphosphates should be provided in sufficient concentration in the oral environment to effect the desired whitening and remineralizing of teeth without toxicity or other undesirable effects. Such compositions may additionally contain a source of fluoride ions to enhance further remineralization. In this manner, compositions of the present invention advantageously achieve both whitening and remineralization of teeth.

Exemplary calcium peroxyphosphate compounds of the present invention include calcium peroxyphosphates, which embrace calcium peroxymonophosphates, calcium peroxydiphosphates, calcium peroxytriphosphates, etc. Other exemplary compounds of the present invention also include calcium diperoxyphosphates, which embrace calcium diperoxymonophosphates, calcium diperoxydiphosphates, calcium diperoxytriphosphates, etc. Overall, compounds of the present invention include the calcium salts of phosphate monomers, dimers, and polymers, provided that at least one of the phosphate structural units is oxidized to a peroxyphosphate group (e.g., $PO_5^{-3}$), comprising one peroxy substituent, or to a diperoxyphosphate group (e.g., $PO_6^{-3}$), comprising two peroxy substituents. These peroxyphosphate and diperoxyphosphate groups may also be in their respective hydrogen or dihydrogen forms. Thus, calcium peroxyphosphates and calcium diperoxyphosphates include calcium compounds having hydrogen peroxyphosphate groups ($HPO_5^{-2}$), dihydrogen peroxyphosphate ($H_2PO_5^{-1}$), hydrogen diperoxyphosphate groups ($HPO_6^{-2}$), and/or dihydrogen diperoxyphosphate groups ($H_2PO_6^{-1}$). Furthermore, the calcium peroxyphosphate and calcium diperoxyphosphate compounds of the present invention may also include hydroxyl ($OH^-$) groups that, in addition to the negatively charged peroxyphosphate and peroxydiphosphate groups (whether or not in their hydrogen forms) must be charge-balanced by the positive oxidation state of calcium.

Other exemplary compounds of the present invention include calcium peroxymonophosphates, calcium peroxydiphosphates, calcium diperoxymonophosphates, and calcium diperoxydiphosphates. Preferred are calcium peroxymonophosphate or calcium diperoxymonophosphate compounds having Formula (I):

$$Ca_qH_x(PHOS)_y(OH)_z \qquad (I)$$

wherein q is $\frac{1}{2}\cdot(3y+z-x)$; x is from 0 to 8; y is an integer from 1 to 3; z is from 0 to 1; x<3y; and PHOS is peroxymonophosphate having the formula $PO_5$ or diperoxymonophosphate having the formula $PO_6$, or calcium peroxydiphosphate or calcium diperoxydiphosphate compounds having Formula (II):

$$Ca_qH_x(DIPHOS) \qquad (II)$$

wherein q is $\frac{1}{2}\cdot(4-x)$; x is from 0 to 3; and DIPHOS is peroxydiphosphate having the formula $P_2O_8$ or diperoxydiphosphate having the formula $P_2O_9$.

Exemplary peroxymonophosphates of the above-defined Formula (I) include $CaHPO_5$, $Ca(H_2PO_5)_2$, $Ca_3(PO_5)_2$, $Ca_4H(PO_5)_3$, and $Ca_5(PO_5)_3OH$. Exemplary peroxydiphosphates of the above-defined Formula (II) include $CaH_2(P_2O_8)$ and $Ca_2(P_2O_8)$.

In one synthesis route in preparing calcium peroxymonophosphate compounds of the present invention, an initial step involves the preparation of peroxymonophosphoric acid. The synthesis of peroxymonophosphoric acid may be carried out as described, for example, by Schmidlin and Massini (Ber., 43, 1910, page 1162) according to the reaction $$P_2O_5 + 2H_2O_2 + H_2O \rightarrow 2H_3PO_5 \qquad (1)$$

However, due to the inherent safety risk of the above highly exothermic reaction (1), improvements in this basic synthesis route to peroxymonophosphoric acid were developed and described, for example, in Can. J. Chem. 81:156-160 (2003) and U.S. Pat. Nos. 3,036,887 and 3,085,856. Alternative methods for preparing this acid are described, for example, by J. E. Such, "Peroxophosphoric Acid & Peroxophosphates" in MELLOR'S COMPREHENSIVE TREATISE ON INORGANIC AND THEORETICAL CHEMISTRY, Vol. VIII (Supp III), Longmana, London (1971). These methods include (i) the hydrolysis of peroxydiphosphate in a strong acid solution, (ii) the reaction of $H_4P_2O_7$ with aqueous hydrogen peroxide, and (iii) the anodic oxidation of $PO_4^{-3}$ or $P_2O_7^{-4}$.

Diperoxyphosphoric acid, $H_3PO_6$, a starting material in the preparation of calcium diperoxymonophosphate, is less well known than $H_3PO_5$. However, this peroxy acid may be prepared, for example, in a manner similar to that for preparation of $H_3PO_5$, namely by the action of hydrogen peroxide on either $P_2O_5$ or pyrophosphoryl chloride ($PO_3Cl_4$). In general, the use of a peroxygenated phosphoric acid starting material allows for the preparation of various types of calcium peroxyphosphate compounds described herein.

Preferably, peroxymonophosphoric acid is prepared according to the above-noted reaction (1) in a water-immiscible liquid medium, such as carbon tetrachloride, that is inert to both the reactants and the reaction product under the conditions of use. The resulting peroxymonophosphoric acid may thereafter be separated from the organic diluent phase by, for example, decantation or equivalent methods. The recovered peroxymonophosphoric acid is then reacted with a calcium compound, preferably selected from the group consisting of calcium carbonate, calcium bicarbonate, calcium hydroxide, and mixtures thereof. The calcium compound may be added as a solid or a solution (e.g., an aqueous solution). The reaction between the peroxy acid and the calcium compound is preferably carried out at low temperature, preferably from about −10° C. to about 20° C., to avoid excessive loss of active oxygen through decomposition. The calcium peroxymonophosphates generated from this reaction typically precipitate rapidly upon mixing of the reactants. When a solid calcium carbonate reactant is used, the rate of dissolution of this compound and the rate of evaporation of carbon dioxide both influence the rate of product precipitation.

The solid product can be recovered from the liquid medium described above by separation methods that include, but are not limited to, evaporation, filtration, and freeze-drying. Product purity can be increased by recrystallization or fractional crystallization, with either of these methods preferably employing water or a mixture of water and a water-soluble organic solvent. Preferred organic solvents having some water solubility and that are appropriate for this purpose include saturated aliphatic ketones (e.g., acetone) and aliphatic alcohols (e.g., methanol, ethanol, and glycerol). The various calcium peroxyphosphate compounds described herein (e.g., calcium peroxydiphosphates, and calcium diperoxydiphosphates) may be prepared following analogous procedures, using the appropriate starting peroxy acid.

While the above-noted procedures may generate a single calcium peroxyphosphate compound, generally a mixture of compounds is obtained. For example, a mixture of the peroxygenated forms $Ca(H_2PO_5)_2$ and $CaHPO_5$ may be obtained in the preparation of calcium peroxymonophosphates. The procedures described above may also yield non-peroxygenated calcium phosphates such as mono- and di-calcium phosphates. Preferably, however, the peroxygenated forms will be present, in either the impure or purified reaction products described above, in an amount of at least about 10% by weight, and more preferably in an amount from about 10% to about 90% by weight, relative to the total amount of peroxygenated and non-peroxygenated calcium phosphates. Mixtures of calcium peroxyphosphates and calcium phosphates may be characterized according to their overall relative amounts of calcium, phosphate, and peroxide and/or according to other analytically identifiable criteria, in order to help assess the types and relative amounts of the calcium phosphate species present. In case a mixture of various calcium peroxyphosphates or a mixture of calcium peroxyphosphates and calcium phosphates is obtained, the molar average calcium to phosphate molar ratio (Ca/P ratio) of the various these calcium compounds ranges preferably from about 0.25 to about 1.67, depending on the relative amounts of calcium compounds and peroxymonophosphoric acid used in the reaction described above. Importantly, both the peroxygenated and non-peroxygenated calcium phosphates, obtained from the synthesis procedures described above, may also be incorporated into dental compositions or restoratives as described herein without the need to segregate the peroxygenated forms. It is also possible to employ precursors of calcium peroxyphosphates (e.g., components comprising sources of calcium and peroxyphosphate that react to form the desired calcium peroxyphosphates) in these restorative compositions, for example in separate compositions that are mixed before or during use. In this manner, the calcium peroxyphosphate compound may be generated in situ within, and/or on the surfaces of, the teeth.

Any of the calcium peroxyphosphates and calcium diperoxyphosphates described above may be in their respective hydrated or peroxyhydrated forms without adversely affecting their ability to release calcium ions, phosphate ions, and peroxide. As is known in the art, hydrated or peroxyhydrated forms refer to the parent molecules having one or more water molecules or hydrogen peroxide molecules, respectively, in their structures. Thus, as an example, a hydrated form of tricalcium peroxymonophosphate may be represented as $Ca_3(PO_5)_2 \cdot mH_2O$, indicating the association of "m" water molecules per molecule of calcium peroxymonophosphate. Likewise, a peroxyhydrated form of tricalcium peroxymonophosphate may be represented as $Ca_3(PO_5)_2 \cdot nH_2O_2$, indicating the association of "n" hydrogen peroxide molecules per molecule of calcium peroxymonophosphate. Typically, "m" is an integer from 0 to 5.

Advantageously, when used in dental compositions the calcium peroxyphosphate compounds described above can readily provide both tooth whitening and remineralizing activity, as they comprise both peroxyphosphate ions and calcium ions in a single molecule of an ionic salt. Thus, these compounds are capable of releasing calcium ions, phosphate ions, and active oxygen simultaneously, in close proximity, and in amounts sufficient and effective for these purposes. By "active oxygen" is meant atomic oxygen (O) that may be generated by the decomposition or hydrolysis of peroxyphosphate ions. As illustrated below, peroxymonophosphate ion, for example, may decompose to yield phosphate and active oxygen according to the following reaction (2):

$$PO_5^{-3} \rightarrow PO_4^{-3} + O \qquad (2)$$

Alternatively, and generally to a lesser extent, peroxymonophosphate ion may react with water (i.e., hydrolyze) to form hydrogen peroxide, which in turn degrades to form active oxygen, as illustrated in the following reactions (3):

Without being bound by theory, it is believed that, as active oxygen is generated according to the reactions (2) and (3) above, a free perhydroxyl radical (HOO.) forms for brief periods of time sufficient to oxidize dental stains. At the same time, calcium ions and phosphate ions deposit or precipitate, as calcium orthophosphate, in the void left behind, thereby remineralizing the tooth, strengthening it, inhibiting its decay, and/or attenuating its sensitivity. Additionally, remineralization, effected by the calcium and phosphate sources, can decrease tooth porosity resulting from the stain removal process. This in turn may prevent or slow the re-formation of a new stain within the void and also prolong the whitening effect. Because the deposited calcium orthophosphate is itself white, remineralization may further enhance whitening. Also, the precipitation of calcium orthophosphate onto and/or into the tooth surface can close pores in enamel and plug dentin tubules (e.g., at root ends) to reduce or eliminate post-treatment tooth sensitivity. The accompanying reduced porosity and/or plugging of dentin tubules can also generally reduce tooth surface permeability and consequently minimize the undesired effect of peroxide diffusion into the tooth pulp.

Associated with the present invention is the determination that sufficiently high concentrations of calcium ions and phosphate ions are particularly effective for tooth remineralization as a means to compensate for the reduction in tooth surface integrity that may result from whitening or bleaching with active oxygen, generated according to above-noted reactions (2) and/or (3).

Compounds of the present invention typically decompose in aqueous media (e.g., upon exposure to saliva) to provide tooth whitening and remineralizing at combined effective amounts or concentrations of calcium ions, phosphate ions, and active oxygen. By "whitening and remineralizing at combined effective amounts" is meant that the amounts of calcium ion, phosphate ion, and active oxygen together are sufficient to whiten teeth and compensate, through precipitation (i.e., remineralization) of calcium phosphate, for some or all of the void that typically accompanies the whitening or stain removal process. The remineralization that is effected by compounds of the present invention also refers to the strengthening of pre-existing tooth weaknesses that are not associated with contemporaneous whitening or stain removal.

Preferably, when used in dental compositions, compounds of the present invention are present, on an anhydrous basis, in the composition in an amount of at least about 1% and preferably from about 3% to about 32% by weight, to provide generally effective amounts of calcium ions, phosphate ions, and active oxygen to effect the dual purposes of tooth whitening and remineralization discussed above. Also additional sources of peroxide, calcium salts, and phosphate salts can be included. In a preferred embodiment, dental compositions of the present invention further comprise a fluoride ion source, believed to promote or catalyze precipitation (remineralization) of the calcium ions and phosphate ions released from compounds of the present invention. The fluoride ion source may be a fluoride compound including, but not limited to, sodium fluoride, potassium fluoride, zinc fluoride, stannous fluoride, zinc ammonium fluoride, sodium monofluorophosphate, sodium hexafluorosilicate, potassium monofluorophosphate, laurylamine hydrofluoride, diethylaminoethyloctoylamide hydrofluoride, 1-ethanol-2-hexadecylimidazoline dihydrofluoride, dodecyltrimethylammonium fluoride, tetraethylammonium fluoride, didecyldimethylammonium fluoride, cetylpyridinium fluoride, dilaurylmorpholinium fluoride, N-carboxymethyl-N-dodecyldiethylammonium fluoride, sarcosine stannous fluoride, glycine potassium fluoride, glycine hydrofluoride, sodium monofluorophosphate and mixtures thereof. Preferred sources of fluoride ion include sodium fluoride, potassium fluoride, sodium monofluorophosphate, and sodium hexafluorosilicate. If used, the fluoride source is present in the composition in an amount, based on fluorine, from about 10 ppm to about 0.5% by weight. The carrier and optionally additives, described below, are generally present in a combined amount from about 10% to about 95% by weight.

The decomposition of peroxymonophosphates according to reaction (2) above, which promotes the effects of tooth whitening and remineralization when used in dental compositions or restoratives, increases in rate with increasing pH, until a maximum decomposition rate is achieved in a pH range of 12-13. In order to inhibit decomposition prior to use, however, these compounds are preferably stabilized by maintaining them either at a neutral pH or at a slightly acidic pH and optionally in the presence of a stabilizer. While low pH favors the hydrolysis of peroxyphosphate according to reaction (3) above, it is believed that the extent of hydrolysis becomes appreciable only under strongly acidic conditions, which are easily avoided.

Stabilizers for use in dental compositions comprising compounds of the present invention include chelating agents that can scavenge and inactivate trace metals that could otherwise catalyze the decomposition process. Suitable chelating agents are described, for example, in U.S. Pat. No. 6,221,341. Metals, such as iron, manganese, and copper, and their oxides are known in the art to promote the degradation of peroxide through Fenton-type reactions. This particular degradation mechanism is undesirable in that the hydroxyl free radical (HO.) is created and is not as effective as active oxygen generated according to reactions (2) and (3) above, in attacking chromogens that stain the teeth.

Stabilizers therefore include, but are not limited to, pharmaceutically acceptable chelating agents such as the various amino carboxylate compounds that have the capacity to form metal-ligand complexes with one or more transition metal ions in solution. Such amino carboxylates include ethylenediaminetetraacetic acid (EDTA) and diethyltriaminepentaacetic (DTPA), 1,2-bis(2-aminophenoxy)ethane-N,N,N', N'-tetraacetic acid (BAPTA), ethylene glycol-bis(2-aminoethyl)-N,N,N',N'-tetraacetic acid (EGTA), and other amino carboxylate compounds having one or multiple carboxylate groups. Any derivative salt form of these amino carboxylate chelating agents, for example the disodium salt form, may be also used, provided that some capacity remains for the chelating agent to complex with free transition metal ions present. Forms of these chelating agents other than salt forms are also effective and include the various ester, anhydride, and halogenated forms of these compounds. A preferred stabilizer is EDTA.

As stated, calcium peroxyphosphate compounds of the present invention may be stabilized under neutral to slightly acidic pH conditions. When used in dental compositions, these compounds can be conveniently decomposed at the time of use to effect the beneficial release of (i) active oxygen for tooth whitening and (ii) calcium phosphate for tooth remineralization. Peroxyphosphate decomposition according to reaction (2) above is achieved, for example, by increasing pH or introducing activators such as catalytic amounts of trace metal ions into the calcium peroxyphosphate composition. A further advantage associated with effecting decomposition by increasing pH is the simultaneous promotion, at elevated pH, of the precipitation of calcium phosphate as tooth mineral. As described previously, calcium phosphate is a decomposition product of calcium peroxymonophosphates.

Based on the above, a kit comprising two separate compositions represents a possible vehicle for employing compounds of the present invention, allowing for long-term storage of these compounds prior to use and activation of these compounds at the point of use. In such an embodiment, for example, the first composition may be a pH-control composition having an alkaline pH and the second composition may comprise a compound of the present invention. In this embodiment, an alkaline pH of the first composition refers to a pH value preferably above 8, and more preferably from about 8 to about 12, and even more preferably from about 9 to about 11. The second composition comprising the calcium peroxyphosphate preferably has a neutral pH or a slightly acidic pH value (e.g., from about 3 to about 7).

Alternatively, the first composition may comprise an activator (e.g., a transition metal ion such as $Zn^{+2}$) to catalyze or accelerate the decomposition of calcium peroxyphosphate upon contact therewith prior to or during use. The first composition may also optionally comprise a soluble calcium salt to provide an additional source of calcium. Soluble calcium salts include, but are not limited to, calcium sulfate (e.g., plaster of paris), calcium chloride, calcium nitrate, calcium acetate, calcium bromide, calcium gluconate, calcium benzoate, calcium glycerophosphate, calcium formate, calcium fumarate, calcium lactate, calcium butyrate, calcium isobutyrate, calcium malate, calcium propionate, and calcium valerate. Preferred soluble calcium salts include calcium chloride, calcium nitrate, calcium sulfate, and calcium acetate. Calcium orthophosphates include, but are not limited to, amorphous calcium phosphate (ACP), amorphous calcium phosphate fluoride (ACPF), and amorphous calcium carbonate phosphate (ACCP), which are described, for example, in U.S. Pat. No. 5,037,639.

Upon increasing the pH of the second composition and/or activating it by combining or mixing it with the first pH-control composition having an alkaline pH and/or an activator, not only is active oxygen made available for whitening, but also the released calcium ions and phosphate ions are precipitated as calcium phosphate for remineralization. Another means of realizing the goals of long-term storage of compounds of the present invention and their activation upon use may be through the provision of a layered composition, with separate layers (e.g., gel layers) being maintained under separate conditions and/or having separate compositions as described above. A further alternative method of stabilizing a calcium peroxyphosphate compound prior to use is to maintain it as a solid (either crystalline or amorphous) or a solid suspended in an inert carrier, such as a polyol. The solid form can then be either dissolved in a composition comprising an aqueous carrier at the point of use or applied directed to the surfaces of the teeth. Yet another alternative for stabilization involves lyophilization of the calcium peroxymonophosphate, coupled with reconstitution prior to use.

In the kit embodiment described previously, comprising two compositions, these compositions may be mixed or combined prior to application to the tooth surface, such that the combination/application steps are performed sequentially. In a preferred method of sequential application, for example, the compositions may be mixed and thereafter applied to the teeth in a tray and/or mouth guard. Alternatively, the compositions may be mixed on the teeth at the time of application (i.e., use) to the teeth in a simultaneous manner. Thus, simultaneous mixing and application includes methods wherein the first composition is applied onto the surface of the teeth (e.g., applying a solution with a cotton tip) and the second composition is then applied and combined with the applied first composition.

Simultaneous mixing and application represents a preferred method of teeth whitening and remineralization, particularly when a first composition that comprises a soluble calcium salt is first applied to the surface of the teeth, allowing the applied calcium to diffuse into the teeth. After application of the first composition, a second composition comprising a compound of the present invention (i.e., a calcium peroxyphosphate) is thereafter applied to the teeth. In this manner, both within the teeth as well as on the surface of the teeth, active oxygen (obtained from the second composition) is generated for whitening or bleaching and the calcium ions (obtained from both compositions) and phosphate ions (obtained from the second composition) are activated for precipitation or remineralization as calcium phosphate tooth mineral. Preferably, the first composition is an aqueous solution. In another preferred embodiment, the second composition is in a gel form and is applied using a tray. In other embodiments, the calcium peroxyphosphate of the second composition may either be suspended as a solid in a non-aqueous medium or otherwise dissolved therein. In yet other embodiments, the second composition may comprise a peroxyphosphate and optionally a non-peroxygenated phosphate, such that the soluble calcium salt of the first composition reacts with the peroxyphosphate of the second composition to generate a calcium peroxyphosphate compound in situ. Without being bound by theory, it is believed that the calcium peroxymonophosphate compounds of the present invention, whether supplied in a single composition, in a kit comprising two or more compositions, or in the form of precursor components that are reacted at the point of use, can cause calcium orthophosphate (or tooth mineral) to precipitate, both on the surfaces of the dental tissues as well as in their interiors.

Whether a single composition, or, as described above, two or more separate compositions are employed, the pH of the compositions of the present invention may be maintained or controlled using any pH-control agents and buffer systems known in the art to be suitable for oral compositions. For example, compositions for oral use may be adjusted and maintained at an alkaline pH, preferably at a pH from about 8 to about 12, using hydroxide compounds (e.g., sodium hydroxide) and/or carbonate compounds (e.g., sodium carbonate). Likewise, compositions may be adjusted and maintained for stabilization purposes at approximately neutral or slightly acidic conditions, preferably at a pH from about 3 to about 7 using, for example, inorganic or organic acids including phosphoric acid, benzoic acid, and/or citric acid. Alternatively, dissolved carbon dioxide, for example in a carbonated solution under pressure, may also function as a pH-control agent as well as a carrier for calcium peroxymonophosphate compounds.

Compositions comprising compounds of the present invention may further comprise any carrier (e.g., a polyol) known in the art and/or discussed hereinafter. In a preferred embodiment, an aqueous polyol carrier in the form of a gel is used. Such carriers and carrier forms are preferred, for example, for providing a calcium peroxymonophosphate gel solution. In general, carriers should be substantially toxicologically benign. Such carriers include polyols which include, but are not limited to, sorbitol, propylene glycol, glycerol, lactitol, xylitol, polypropylene glycols, polyethylene glycols, and hydrogenated corn syrup. Oil-based carriers may also be used, especially when combined with a surfactant capable of emulsifying compositions upon contact with water. Such oils include vegetable oils, mineral oils, and essential oils, in addition to their higher molecular weight counterpart waxes and esters. Essential oils have antiseptic and antimicrobial effects, and include thymol, menthol, eucalyptol, and eugenol. Aqueous, alcohol (e.g., ethanol), and nonaqueous polyol (e.g., glycerol) carriers may also be used in combination.

The carrier used in compositions of the present invention may be in any conventional form, including, but not limited to, a toothpaste, a prophylactic paste, a tooth polish, a tooth cleaning abrasive slurry, a gel, a professional gel, a varnish, a self-adhesive strip, a cream, a mouthwash, a pre- or post-brushing dental rinse, a dental spray, a dental cleanser, a dental floss, a floss wax product, a chewing gum, a lozenge, a tablet, a powder, a pumice flour, a polymeric compound, a carbonated solution, an edible food product, and the like. Preferred forms of the compositions include toothpastes, gels, professional gels, varnishes, self-adhesive strips, chewing gums, powders, pumice flour, dental rinses, carbonated solutions, or edible food products. These and other forms are known in the art and described in detail, for example, in U.S. Pat. Nos. 6,303,104 and 5,624,906. Other preferred carrier forms for suspending calcium peroxymonophosphate compounds include gels, chewing gums, powders, varnishes, polymers, mouth rinses, carbonated solutions, and tooth dentifrices. Varnishes have been used for sustained-release tooth fluoridation and are applicable for delivery of the whitening and remineralization compositions of the present invention as well. Tooth varnishes are generally compounds that are topically applied to teeth with a special brush, cotton, or tray and harden over a short time by contact with saliva, air, or both. Varnishes typically comprise a carrier of a natural polymer (e.g., colophony or pine resin) or synthetic polymer (e.g., a polyurethane based resin or a polymethacrylate based resin such as polymethyl methacrylate) in alcoholic solution.

Professional products, such as professional gels, are generally intended for application under professional supervision and typically contain higher amounts of active ingredients (e.g., a calcium peroxyphosphate compound) or other whitening agents than those products designed for general consumer use. Professional gels are often applied using, for example, a tray to expose only dental surfaces and not the gums or soft tissues to the compositions. This manner of application is described, for example, in U.S. Pat. No. 6,221,341 along with various thickeners that are advantageously used in compositions for such applications. A preferred mode of application, when a gel or paste is used as a carrier form (whether or not it is considered a professional product), involves the use of such a tray or mouth guard to restrict the contact of the compositions to the teeth. In this type of application and also generally, it may be desirable to apply a composition comprising a compound of the present invention and one or more additional compositions in one or more repetitive steps in a predetermined order (e.g., application of a composition comprising a readily available calcium ion source or a phosphate ion source, followed by application of a composition comprising a calcium peroxyphosphate compound). In this manner and as described above, compounds of the present invention may be stabilized, for example, by long-term storage at neutral or slightly acidic pH and may thereafter be activated at the time of use by mixing with a separate composition at alkaline pH. As stated previously, another method of stabilizing the calcium peroxyphosphate compounds prior to use is to maintain them as a solid (either crystalline or amorphous) or a solid suspended in an inert carrier, such as a polyol. Otherwise, the compounds may also be dissolved or suspended in a nonaqueous carrier such as glycerol. Dissolved or suspended compounds of the present invention and their respective carriers can be applied directly onto the teeth. Solid forms of these compounds may be dissolved in an aqueous or nonaqueous carrier media at the point of use, just prior to application.

The carrier may be in the form of a paste or gel, where the carrier is used in a multi-layer delivery system with two or more distinct compositions contained in separate layers. In this manner, it is also possible to obtain a striped product, wherein colorants of contrasting colors are incorporated in the distinct layer compositions, with the colorants being pharmacologically and physiologically non-toxic in the amounts used. Colorants used for this particular embodiment include both pigments and dyes, as described, for example, in U.S. Pat. No. 6,290,935. The use of colorants for distinct composition layers is not only aesthetically pleasing in many cases but also, where it is desired to mix the compositions thoroughly before use, provides a visual indication of how uniformly mixed the compositions are.

With respect to the various carrier forms described above, a plurality of conventional packaging methods and dispensing containers may be employed and are described, for example, in U.S. Pat. No. 6,303,104. Preferred dispensing containers include tubes, pumps, syringes, and other containers suitable for dispensing a paste, gel, liquid or slurry. Another preferred dispensing system is provided in U.S. Pat. No. 5,902,568, which discloses a pump dispenser having compartments for separately storing components and a means for combining the components as unmixed streams prior to use. In another embodiment, the dispensing container may separate the carrier from the active ingredients and may additionally combine these shortly before use.

Regardless of the carrier, the compositions may contain one or more conventional additives described, for example, in U.S. Pat. Nos. 6,303,104; 6,290,935; 6,221,341; 5,902,568; and 5,624,906. Such additives include, but are not limited to, surfactants (e.g., anionic, cationic, nonionic, and zwitterionic surfactants), cosurfactants or cleansing agents, soaps, flavoring agents, sweetening agents, aroma agents, astringents, anti-plaque agents, anti-calculus agents, anti-bacterial agents (e.g., cetyl pyridinium chloride), preservatives, sudsing agents, humectants, thickening agents (including inorganic thickeners such as hydrated silica), binding agents or cothickeners, coloring or other whitening agents, abrasive polishing agents, alcohols, buffering agents, alkali metal halide salts, desensitizing agents, healing agents, other preventative caries agents, vitamins, amino acids, proteins, opacifiers, antibiotics, anti-enzymes, enzymes, other oxidizing agents, antioxidants, and water. When used, these additives are present in amounts that do not substantially adversely affect the desired stain removal and remineralizing capabilities of compounds of the present invention as discussed above. The particular amounts of the additives used will depend upon the type and form of the carrier.

All references cited in this specification, including without limitation, all papers, publications, patents, patent applications, presentations, texts, reports, manuscripts, brochures, books, journal articles, periodicals, and the like, are hereby incorporated by reference into this specification in their entireties. The discussion of the references herein is intended merely to summarize the assertions made by their authors and no admission is made that any reference constitutes prior art. Applicant reserves the right to challenge the accuracy and pertinence of the cited references. In view of the above, it will be seen that several advantages of the invention are achieved and other advantageous results obtained.

It is intended that all matter contained in this application, including all theoretical mechanisms and/or modes of interaction described above, are illustrative only and not limiting in any way the scope of the present invention or the appended claims.

The following examples are set forth as representative of the present invention. These examples are not to be construed as limiting the scope of the invention as these and other equivalent embodiments will be apparent in view of the present disclosure and appended claims.

EXAMPLE 1

Preparation of Calcium Peroxymonophoshpate

A 9.9 gram sample of phosphorus pentoxide powder was suspended in 68 g of carbon tetrachloride and cooled in an ice bath under vigorous stirring. To this suspension, 5.3 ml of 70% aqueous hydrogen peroxide was added dropwise at rate of 3 drops per second. The mixture was stirred for 3 hrs after the hydrogen peroxide addition. The mixture over time formed separate organic and aqueous peroxymonophosphoric acid layers. Five milliliters of the acid layer was obtained by decanting. To half of this inorganic concentrated peroxymonophosphoric acid, calcium carbonate slurry was added slowly in an ice bath and under stirring, until the pH of the solution was 1.7. This solution was then lyophilized. The resulting solid comprised calcium peroxymonophosphates with a Ca/P ratio of 0.28 and possibly additionally contained non-peroxygenated calcium phosphate compounds. The prepared calcium peroxymonophosphate had a distinct x-ray powder diffraction pattern, different from that corresponding to calcium phosphate. The d-space for 010 was in the range of 12.5 to 12.9 Å, compared to 11.7 Å corresponding to calcium phosphate. The calcium peroxymonophosphates also exhibited a peroxide IR peak of 785 $cm^{-1}$, which was absent from the corresponding calcium phosphates.

EXAMPLE 2

Calcium carbonate slurry was added slowly, under stirring, to the other half of the inorganic concentrated peroxymonophosphoric acid layer as described in the Example 1, until the pH of solution was 3.5. This solution was then lyophilized. The solid comprised calcium peroxymonophosphates with a Ca/P ratio of 0.5 and possibly additionally contained non-peroxygenated calcium phosphate compounds such as dicalcium phosphate dihydrate and monocalcium phosphate monohydrate. The prepared calcium peroxymonophosphate has a distinct x-ray powder diffraction pattern different from that corresponding to calcium phosphate. The d-space for 010 was 12 Å, compared to 11.7 Å for calcium phosphate. The calcium peroxymonophosphates also exhibited a peroxide IR peak of 785 $cm^{-1}$, which was absent from the corresponding simple calcium phosphates.

EXAMPLE 3

Alternate Preparation of Calcium Peroxymonophosphate

Suspend 2.22 grams of calcium hydroxide in 50 ml of water. To this suspension, slowly add 2.28 grams of concentrated peroxymonophosphoric acid, to be prepared as described in Example 1, in order to precipitate calcium peroxymonophosphate. Filter the resulting slurry and wash it with distilled water. The solid to be recovered is a basic calcium peroxymonophosphate, possibly also containing one or more calcium phosphate compounds.

EXAMPLE 4

Preparation of Calcium Peroxydiphosphate

Dissolve 3.46 grams of potassium peroxydiphosphate in 10 ml of water. To this solution, add 2.94 grams of calcium chloride dihydrate under stirring, in order to precipitate calcium peroxydiphosphate. Filter the resulting slurry and wash it with distilled water. The solid to be recovered contains calcium peroxydiphosphate.

EXAMPLE 5

Preparation of Calcium Diperoxymonophosphate

Prepare diperoxymonophosphoric acid by the action of hydrogen peroxide on pyrophosphoryl chloride. Maintain this inorganic diperoxymonophosphoric acid in an ice bath under stirring and slowly add a calcium carbonate slurry until the pH of the resulting solution is 3.3 and calcium diperoxymonophosphate precipitates. Filter the resulting slurry and then wash it with distilled water. The solid to be recovered contains calcium diperoxymonophosphates and possibly also contains one or more calcium phosphate compounds.

What is claimed is:

1. A calcium peroxyphosphate compound or a hydrate or a peroxyhydrate thereof, wherein said calcium peroxyphosphate compound is a calcium peroxymonophosphate or a calcium diperoxymonophosphate compound in solid form and having Formula (I):

$$Ca_q H_x (PHOS)_y (OH)_z \qquad (I)$$

or a hydrate or a peroxyhydrate thereof, wherein q is ½·(3y+z−x); x is from 0 to 8; y is an integer from 1 to 3; z is from 0 to 1; x<3y; and PHOS is peroxymonophosphate having the formula $PO_5$ or diperoxymonophosphate having the formula $PO_6$.

2. The calcium peroxyphosphate compound of claim 1, wherein said compound is a calcium peroxymonophosphate compound.

3. The compound of claim 2, wherein said compound is selected from the group consisting of $CaHPO_5$, $Ca(H_2PO_5)_2$, $Ca_3(PO_5)_2$, $Ca_4H(PO_5)_3$, $Ca_5(PO_5)_3OH$, and hydrates and peroxyhydrates thereof.

4. A tooth whitening and remineralizing composition comprising the calcium peroxyphosphate compound of claim 1 or a hydrate or a peroxyhydrate thereof that releases, in an aqueous environment, calcium ions, phosphate ions, and active oxygen in a combined tooth whitening and remineralizing effective amount.

5. The composition of claim 4, wherein said composition further comprises a pH-control agent.

6. The composition of claim 5, wherein said pH-control agent is a hydroxide compound and said composition has an alkaline pH.

7. The composition of claim 5, wherein said pH-control agent is carbon dioxide and said composition has an acidic pH.

8. The composition of claim 4, further comprising a fluoride ion source.

9. The composition of claim 8, wherein said fluoride ion source is selected from the group consisting of sodium fluoride, potassium fluoride, monofluorophosphate, hexafluorosilicate, and mixtures thereof 10. The composition of claim 4, further comprising a polyol carrier in a gel form.

11. A tooth whitening an remineralizing kit comprising:
(a) a pH-control composition having an alkaline pH, and
(b) the composition of claim 4 having a neutral or acidic pH.

12. The kit of claim 11, wherein said pH-control composition comprises a soluble calcium salt.

13. The kit of claim 11, wherein said pH-control composition is an aqueous solution.

14. A method for whitening and remineralizing teeth, said method comprising applying to said teeth a composition comprising the compound of claim 1 or a hydrate or a peroxyhydrate thereof that releases, in an aqueous environment, calcium ions, phosphate ions, and active oxygen in a combined whitening and remineralizing effective amount.

15. The method of claim 14, wherein said composition is applied using a tray.

16. A method for whitening and remineralizing teeth, said method comprising contacting said teeth with a dental restorative comprising:
(a) the calcium peroxyphosphate compound of claim 1 or a hydrate or a peroxyhydrate thereof, and
(b) a carrier for suspending said calcium peroxyphosphate compound, said hydrate or said peroxyhydrate thereof, wherein said carrier is selected from the group consisting of a gel, a chewing gum, a powder, a varnish, a mouth rinse, a nonaqueous medium, and a carbonated solution,
wherein, during said contacting, active oxygen is released to whiten said teeth and calcium phosphate is precipitated to remineralize said teeth.

17. A method for preparing the calcium peroxyphosphate compound of claim 1 or a hydrate or a peroxyhydrate thereof, said method comprising:
(a) reacting a peroxy acid with a calcium compound to yield said calcium peroxyphosphate compound.

18. The method of claim 17, wherein said calcium peroxyphosphate compound is calcium peroxymonophosphate and said peroxy acid is peroxymonophosphoric acid.

19. The method of claim 17, wherein said calcium compound is selected from the group consisting of calcium carbonate, calcium bicarbonate, and calcium hydroxide.

20. The method of claim 17, wherein said reacting step (a) is carried out at a temperature from about −10° C. to about 20° C.

21. The method of claim 17, further comprising, after said reacting step (a):
(b) recovering said calcium peroxyphosphate compound by a separation method selected from the group consisting of evaporation, filtration, and freeze drying.

22. The method of claim 21, further comprising, after said recovering step (b):
(c) purifying said calcium peroxyphosphate compound by recrystallization or fractional crystallization from water or a mixture of water and a water-soluble organic solvent.

23. The method of claim 22, wherein said water-soluble organic solvent is a saturated aliphatic ketone or an aliphatic alcohol.

* * * * *